United States Patent [19]
Koester et al.

[11] Patent Number: 6,019,472
[45] Date of Patent: Feb. 1, 2000

[54] CONTACT LENS ELEMENT FOR EXAMINATION OR TREATMENT OF OCULAR TISSUES

[76] Inventors: Charles J. Koester, 60 Kent Rd., Glen Rock, N.J. 07452-2041; James E. Roberts, 23946 Ibis Ct., Laguna Niguel, Calif. 92677

[21] Appl. No.: 09/074,402

[22] Filed: May 8, 1998

Related U.S. Application Data

[60] Provisional application No. 60/046,205, May 12, 1997.

[51] Int. Cl.[7] ........................................................ A61B 3/00
[52] U.S. Cl. ............................................................. 351/219
[58] Field of Search ................................... 351/212, 213, 351/214, 219, 221, 205, 206; 359/382, 383, 656; D16/131

[56] References Cited

U.S. PATENT DOCUMENTS

| | | |
|---|---|---|
| 4,270,842 | 6/1981 | Muchel et al. ............................ 351/219 |
| 4,799,784 | 1/1989 | Safir ........................................ 351/212 |
| 4,976,535 | 12/1990 | Reis ........................................ 351/214 |
| 5,032,020 | 7/1991 | Robert ..................................... 351/219 |
| 5,116,115 | 5/1992 | Lange et al. ............................. 351/212 |
| 5,171,254 | 12/1992 | Sher . | |
| 5,359,373 | 10/1994 | Koester et al. . | |
| 5,556,417 | 9/1996 | Sher . | |
| 5,757,464 | 5/1998 | Volk ........................................ 351/219 |

OTHER PUBLICATIONS

Advertisement of Volk Optical, *Ophthalmology*, (1998).
Wilensky, "Optics of Gonioscopy", *Clinical Ophthalmology*, vol. 1, Chap. 62, pp. 3 and 4 (1990).
Auran et al., "Wide field Scanning Slit in Vivo Confocal Microscopy of Flattening–Induced Corneal Bands and Ridges", *Scanning*, vol. 16, pp. 182–186 (1994).
Koester et al., "Clinical Microscopy of the Cornea Utilizing Sectioning and a High–Numerical–Aperture Objecxtive", *J. Opt. Soc. Am. A,* vol. 10, No. 7 (1993).
"Stop a Moving Target", advertisement from eyeFix™, Inc.

*Primary Examiner*—George Manuel
*Attorney, Agent, or Firm*—Greenblum & Bernstein, P.L.C.

[57] ABSTRACT

Multi-layered contact lens element for at least one of examination and treatment of ocular tissues. The multi-layered contact lens element includes a plurality of lens elements in layers including a first lens element having a recess capable of holding a volume of liquid against a cornea of an eye to be examined or treated. Contact lens element for at least one of examination and treatment of ocular tissues includes a lens including a contact surface and an exterior convex surface, the contact surface including a protruding contact ring which forms a recess which is capable of providing a volume for liquid between the lens and a cornea of an eye to be examined or treated when the protruding contact ring is in contact with the cornea. A system for at least one of examination and treatment of ocular tissues includes: an optically clear liquid having a refractive index greater than 1.338; and a contact lens element capable of holding the liquid against a cornea of an eye to be examined or treated. A system for at least one of examination and treatment of ocular tissues includes: a liquid; a contact lens element having a recess capable of holding a volume of the liquid against a cornea of an eye to be examined or treated; and a microscope connected to the contact lens element. A system for examining ocular tissue includes: a microscope having at least one lens including an external lens; and a transparent, malleable material attached to the external lens of the microscope, the malleable material being capable of contacting and conforming to a cornea of an eye to be examined or treated. Methods for using the contact lens elements.

82 Claims, 6 Drawing Sheets

CONTACT LENS ELEMENT FOR EXAMINATION OR TREATMENT OF OCULAR TISSUES

CROSS-REFERENCE TO RELATED APPLICATION

The present application claims the priority under 35 U.S.C. §119(e) of U.S. Provisional Application No. 60/046,205, filed May 12, 1997, the disclosure of which is expressly incorporated by reference herein in its entirety. The present application expressly incorporates by reference herein the entire disclosure of U.S. Provisional Application No. 60/084,789, entitled "Contact Lens Element and System for Examination or Treatment of Ocular Tissues", which is filed on even date with the present application.

BACKGROUND OF THE INVENTION

1. Field of the Invention

The present invention may involve reducing or eliminating aberrations produced by an irregularly shaped cornea surface during examination or treatment of the eye. This invention also relates to apparatus and methods for stabilizing the position of the eye during examination or treatment procedures.

2. Discussion of Background

The cornea is a transparent tissue that not only allows transmission of light into the eye, but also provides most of the optical power for focusing light on the retina, the image sensing portion of the eye. The crystalline lens, located approximately 4 mm behind the cornea, provides the additional optical power needed to focus the image precisely at the retina.

Corneas are aspheric, in that the curvature is greatest at the center and less toward the periphery. Most corneas also have some astigmatism, i.e., greater curvature in one azimuthal direction than in the perpendicular direction. The irregular shape of the eye affects the path of light through the eye. This aberration in the light path may be corrected by spectacles or contact lenses.

Further, almost all corneas, when measured carefully, have some degree of irregular astigmatism. In irregular astigmatism, irregularities in the shape of the cornea cannot be optically corrected by a combination of spherical and optical elements.

One way to reduce the effects of astigmatism involves use of contact lenses. A rigid, i.e., non-flexible, contact lens will generally have a layer of tears between the lens and the cornea, the thickness of which will vary from center to edge. The layer of tears improves the image which reaches the retina because the refractive index of the tears (1.336) is closer to the refractive index of the cornea (1.376) than the refractive index of air (1.0). Thus, when a rigid contact lens is used, variations in cornea topography have less effect on light rays than they would when the cornea is in air. As a result, the optical effects of corneal irregularity are significantly reduced. However, if the cornea astigmatism is sufficiently large, there will be residual astigmatism due in part to the fact that the refractive index of the tear layer does not exactly match that of the cornea. Further, there may be astigmatism in the crystalline lens or other irregularity in the crystalline lens.

As a result, for many years, contact lenses have been used with patients having irregular corneas, particularly corneas having high levels of astigmatism. A hard contact lens with a spherical back surface is prescribed, and the tear layer between the back surface and the cornea reduces the aberrations of the cornea by a factor of about:

$$\frac{n_{cornea} - n_{tears}}{n_{cornea} - n_{air}} = \frac{1.376 - 1.336}{1.376 - 1.0} = \frac{0.040}{0.376} = 0.106$$

That is, the aberrating effect of an irregular cornea is reduced to about 10% of that for the cornea in air.

Taking into consideration the known methods for correcting vision, there are several known techniques for facilitating the treatment or examination of the eye. Biomicroscopes, also known as slit lamps, are often used with a diagnostic contact lens which is hand-held against the cornea, utilizing a viscous liquid such as a methylcellulose solution to form an optical coupling to the cornea.

This procedure for using diagnostic contact lenses reduces the aberrations that would be produced by the same cornea in air. The layer of methylcellulose solution reduces the effects of astigmatism because the refractive index of the methylcellulose solution (1.337) is closer to the refractive index of the cornea (1.376) than the refractive index of air (1.0). As a result, variations in cornea topography have less effect on light rays than they would when the cornea is in air.

Examples of diagnostic contact lenses which are used in conjunction with biomicroscopes include diagnostic contact lenses made by Ocular Instruments, Inc. and Volk Optical Co. These contact lenses are hand-held lenses with concave front surfaces to contact the cornea, generally used with a viscous liquid such as methylcellulose solution. Some of these lenses are gonio-lenses which include inclined mirror surfaces that allow examination of various regions of the retina and the region called the angle of the anterior chamber. FIG. 5 of WILENSKY, "Optics of Gonioscopy", *Clinical Ophthalmology*, Vol. 1 (1990), shows how the gonio-lenses contact the eye, and how a ray of light travels from the angle recess of the eye to the mirror surface and then out of the lens.

U.S. Pat. No. 5,359,373 to KOESTER et al., the disclosure of which is herein incorporated by reference in its entirety, discloses a contact lens element with a flat front surface for contacting the cornea to stabilize the longitudinal position of the cornea. Because the contact lens element flattens the portion of the cornea against which it is pressed, the contact lens element helps to reduce aberrations caused by the normal, unflattened shape of the cornea. Column 5 of this document discloses that small variations from flatness can be utilized, and discloses that if the surface is concave with a radius of curvature less than that of the cornea, it is possible to trap air bubbles in the tear layer between the element and the cornea, thereby disrupting the optical continuity of the system. Column 7 of this document indicates that while a concave contact surface might have optical advantages, it could possibly cause a greater distortion of the cornea if it is not precisely aligned with the axis of the cornea. The flat contact lens element, while useful for examining the cornea, is not suitable for examination of the crystalline lens and details at other depths within the eye. The flattening of the cornea has the effect of causing wrinkles, which show up as a corneal mosaic as discussed in AURAN et al., "Wide Field Scanning Slit in vivo Confocal Microscopy of Flattening-Induced Corneal Bands and Ridges", *Scanning*, Vol. 16, pp. 182–86 (1994). These wrinkles produce inhomogeneities in the optical path through the cornea and have been observed to result in a blurring of the retinal image during examination at high magnification.

KOESTER et al., "Clinical Microscopy of the Cornea Utilizing Optical Sectioning and a High-Numerical- Aperture Objective", *J. Opt. Soc. Am. A*, Vol. 10, No. 7 (July 1993), the disclosure of which is herein incorporated by reference in its entirety, discloses contact lens elements similar to those disclosed in U.S. Pat. No. 5,359,373 to KOESTER et al. This article discloses that a slightly concave surface can be used for the contact lens element, as long as the radius of curvature is greater than that of the cornea, to reduce the possibility of trapping air bubbles between the element and the cornea.

SUMMARY OF THE INVENTION

It is an object of the present invention to provide a contact lens element which reduces aberrations produced by an irregularly shaped cornea.

It is an object of the present invention to provide a contact lens element that increases the numerical aperture (NA) of long working distance objectives.

It is another object of the present invention to provide a contact lens element that corrects chromatic and spherical aberrations.

It is another object to provide a contact lens element that increases the resolution and magnification of a microscope objective.

It is another object of the present invention to provide a contact lens element having a contact surface that contacts the eye to help stabilize the eye during examination or treatment.

It is another object to provide a contact lens element and microscope system in which the contact lens element is optically corrected so as to optimize the optical image.

It is an object of the present invention to provide a contact lens element, liquid, and microscope system in which the contact lens element is optically corrected so as to optimize the optical image.

The present invention is directed to a system which includes a contact lens element and a liquid that fills a space between the contact lens element and the cornea of an eye to be treated or examined. Where the outer surface of the cornea has astigmatism or irregular astigmatism, the aberrating effect on the light rays passing through the cornea can be minimized if the indices of refraction of the liquid and cornea are equal or nearly equal. Thus, the contact lens element and the liquid provide an optical link between the eye and an optical instrument, e.g., a microscope, that is used to examine or treat the eye.

The present invention is also directed to a contact lens element that is made of a soft or malleable material. The soft or malleable contact lens element may be resilient and may have a concave contour, which resilient material may be supported by a glass or plastic substrate. The malleable material may be either adhesive or attachable to the front lens of an optical microscope and soft or malleable enough to conform to the exact shape of a cornea without significantly distorting the shape of the cornea.

The present invention is also directed to a system involving a contact lens element having concave and convex surfaces and a structure for mounting the contact lens element to a microscope in order to optically couple the convex surface of the contact lens element to an objective lens of the microscope. The mounting structure may include structure for selectively adjusting the distance between the microscope objective lens and the convex surface of the contact lens element to allow focusing. The contact lens element may comprise separate pieces and the distance between these separate pieces may be adjusted to adjust the focal depth.

The present invention is also directed to a system including an external lens which is either connected to a microscope objective or forms part of a microscope objective, a bellows connected to at least one of the external lens and the microscope objective, and a hollow tube connected to the bellows. A fluid is disposed in a space formed by the external lens, the bellows, and a cornea of an eye to be examined or treated. The focal plane of the system may be adjusted by moving the external lens. As a result, the thickness of the fluid between the external lens and the cornea is varied.

In accordance with one aspect, the present invention is directed to a multi-layered contact lens element for at least one of examination and treatment of ocular tissues, comprising a plurality of lens elements in layers including a first lens element having a recess capable of holding a volume of liquid against a cornea of an eye to be examined or treated.

In accordance with another aspect, the recess has a concave surface having a radius of curvature less than about 8 mm.

In accordance with yet another aspect, the contact lens element includes a hole therethrough for injecting a liquid into a space between the contact lens element and the cornea when the contact lens element is in contact with the cornea. The contact lens element may also include a vent.

In accordance with still another aspect, the plurality of lens elements further comprises a second lens element attached to the first lens element, and a third lens element attached to the second lens element, with the third lens element having an exterior convex surface.

In accordance with another aspect, the contact lens element comprises at least one material selected from the group consisting of glass and plastic.

In accordance with yet another aspect, the first lens element comprises a rim which is capable of contacting the cornea.

In accordance with still another aspect, the contact lens element comprises a plurality of separate pieces.

In accordance with another aspect, the contact lens element comprises a microscope objective.

In another aspect, the present invention is directed to a contact lens element for at least one of examination and treatment of ocular tissues, comprising a concave surface capable of contacting a cornea of an eye to be examined or treated having a radius of curvature that is less than approximately a radius of curvature of the cornea and having a diameter of about 7 to 12 mm, and an exterior convex surface having a diameter of about 13 to 19 mm, the contact lens element having a thickness of about 8 to 20 mm, wherein the contact lens element includes a hole therethrough for injecting a liquid into a space between the contact lens element and the cornea when the contact lens element is in contact with the cornea, and wherein the contact lens element includes a vent.

In still another aspect, the present invention is directed to a contact lens element for at least one of examination and treatment of ocular tissues, comprising a lens including a contact surface and an exterior convex surface, the contact surface comprising a protruding contact ring which forms a recess which is capable of providing a volume for liquid between the lens and a cornea of an eye to be examined or treated when the protruding contact ring is in contact with the cornea.

In yet another aspect, the present invention is directed to a system for at least one of examination and treatment of ocular tissues, comprising: an optically clear liquid having a refractive index greater than 1.338; and a contact lens element capable of holding the liquid against a cornea of an eye to be examined or treated.

In accordance with another aspect, the liquid has a refractive index of about 1.366 to 1.386.

In accordance with yet another aspect, the liquid comprises an aqueous solution. The aqueous solution may be a salt solution such as sodium chloride solution. The aqueous solution may be an organic solution which includes a protein such as albumin and gelatin. The aqueous solution may comprise a sugar solution which includes a sugar such as dextrose, sucrose, glucose, and maltose.

In accordance with another aspect, the contact lens element comprises a part of an imaging system for examining structures within an eye. The imaging system may comprise a microscope. The contact lens element may be rigidly attached to and aligned with the imaging system.

In accordance with another aspect, the present invention is directed to a system for at least one of examination and treatment of ocular tissues, comprising: a liquid; a contact lens element having a recess capable of holding a volume of the liquid against a cornea of an eye to be examined or treated; and a microscope connected to the contact lens element.

In accordance with yet another aspect, the present invention is directed to a system for examining ocular tissue, comprising: a microscope having at least one lens comprising an external lens; and a transparent, malleable material attached to the external lens of the microscope, the malleable material being capable of contacting and conforming to a cornea of an eye to be examined or treated.

In accordance with another aspect, the malleable material comprises an optically homogeneous, biocompatible substance which has a refractive index of about 1.366 to 1.386. The malleable material may comprise at least one material selected from the group consisting of sodium hyaluronate and methylcellulose solution.

In accordance with yet another aspect, the malleable material comprises a resilient material having a concave surface for contacting the cornea. The resilient material may comprise a contact lens comprising water. The resilient material may be connected to the external lens of the microscope via a substrate. The substrate may comprise at least one material selected from the group consisting of plastic and glass.

In accordance with another aspect, the present invention is directed to a system for at least one of examination and treatment of ocular tissues, comprising: a microscope objective; a lens associated with the microscope objective; a hollow tube including an open end adapted to contact a cornea of an eye to be examined or treated; an adjustable chamber at the open end of the hollow tube, the adjustable chamber being defined by a movable wall member, a portion of the hollow tube, and an opening forming the open end of the hollow tube, the lens comprising a portion of the movable wall; and at least one aperture associated with the adjustable chamber for introducing a variable volume of liquid into the adjustable chamber when the opening is placed against the cornea.

In accordance with yet another aspect, the lens is connected to the microscope objective.

In accordance with still another aspect, the lens forms a part of the microscope objective.

In accordance with another aspect, the system further comprises a fine focus mechanism capable of adjusting a position of the microscope objective relative to the cornea.

In accordance with another aspect, the system further comprises a reservoir associated with the at least one aperture.

In accordance with another aspect, the system may further comprise a fine focus mechanism capable of adjusting a position of the microscope objective relative to the cornea.

In accordance with another aspect, the present invention is directed to a method for at least one of examining and treating ocular tissue. The method includes: providing a contact lens element associated with a microscope, the contact lens element having a recessed surface; placing the contact lens element on the cornea to form a substantially enclosed space between the recessed surface of the contact lens element and the cornea; at least one of filling the substantially enclosed space with liquid and allowing the substantially enclosed space to become filled with liquid; and at least one of examining and treating ocular tissue by light transmission through the liquid and the contact lens element.

In accordance with one aspect, the substantially enclosed space is filled with liquid by using a hypodermic needle that is inserted into a hole in the contact lens element which leads from an outside to the substantially enclosed space, and wherein the contact lens element includes a vent.

In accordance with another aspect, the at least one of examining and treating of the ocular tissue comprises examining a crystalline lens, an iris, and/or a retina.

In accordance with yet another aspect, the at least one of examining and treating of ocular tissue comprises using a laser. The laser may comprise a laser photocoagulator or a laser photodisrupter.

In accordance with still another aspect, the at least one of examining and treating of ocular tissue comprises employing adaptive optics to improve images of internal eye structures.

In accordance with another aspect, the present invention is directed to a method for at least one of examining and treating ocular tissue, comprising: attaching a transparent, malleable material to a lens of a microscope; contacting the malleable material with a cornea; and at least one of examining and treating ocular tissue by light transmission through the malleable material.

BRIEF DESCRIPTION OF THE DRAWINGS

The present invention is further described in the detailed description which follows, in reference to the noted non-limiting drawings, wherein.

DETAILED DESCRIPTION OF THE INVENTION

Figure 1:
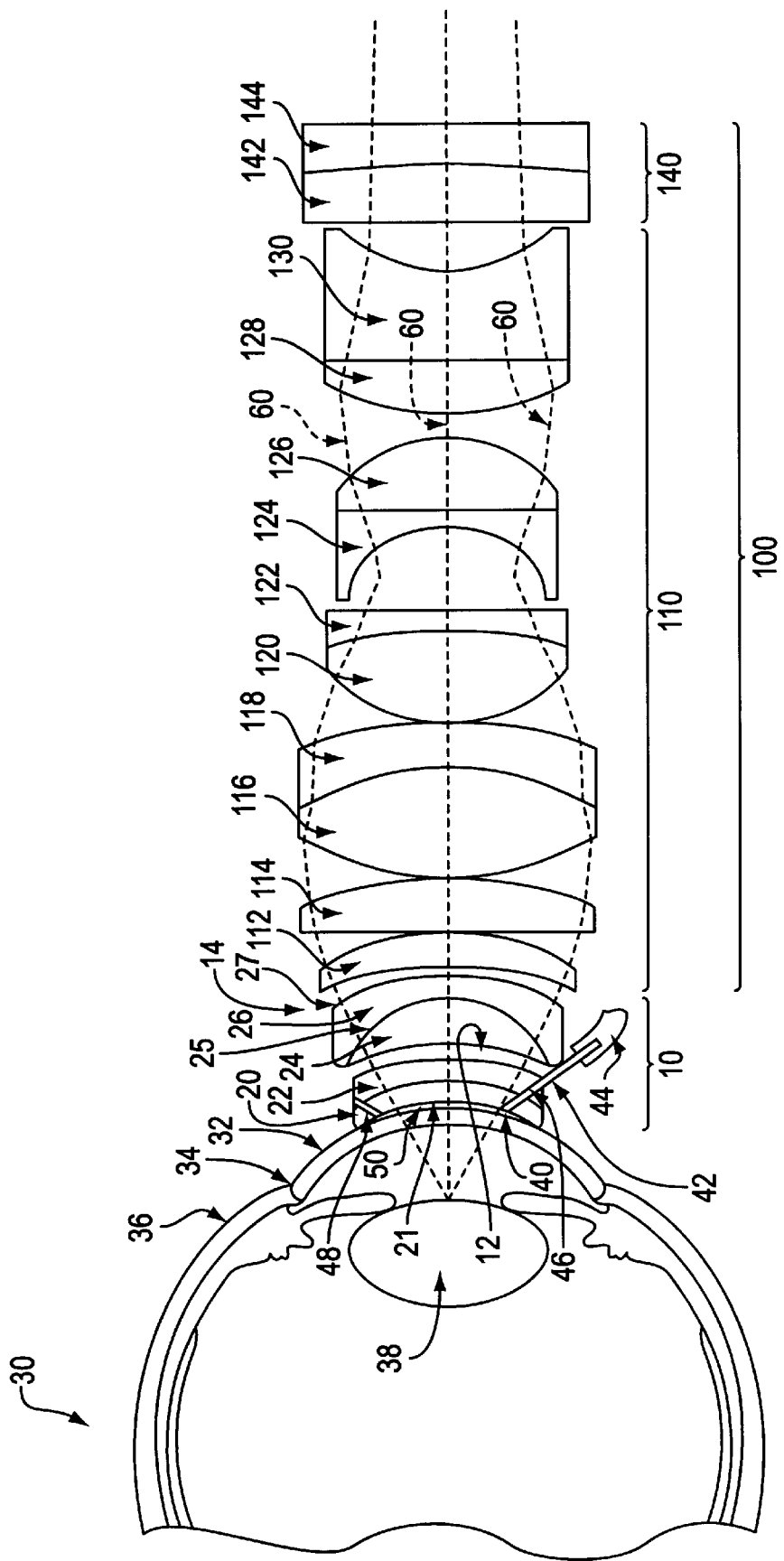
FIG. 1 is a schematic of an eye to be treated or examined as well as a contact lens element and microscope system according to the present invention.

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description taken with the drawings making apparent to those skilled in the art how the several forms of the invention may be embodied in practice.

All percent measurements in this application, unless otherwise stated, are measured by weight based upon 100% of a given sample weight. Thus, for example, 30% represents 30 weight parts out of every 100 weight parts of the sample.

Unless otherwise stated, a reference to a compound or component, includes the compound or component by itself, as well as in combination with other compounds or components, such as mixtures of compounds.

Unless otherwise stated, all refractive indices are measured with light having a wavelength of 587.6 nm.

Before further discussion, a definition of the following terms will aid in the understanding of the present invention.

MICROSCOPE: device comprising an objective lens and at least one of an eye piece lens and an image capturing device such as photographic film or a CCD camera.

NUMERICAL APERTURE (NA): a measure of the power of a microscope objective, equal to the product of the refractive index of the medium at the front focal plane of the objective and the sine of the angle between the optical axis and outermost ray in the medium at the focal plane.

SACCADE: a rapid intermittent eye movement, as one that occurs when the eye fixes on one point after another in the visual field.

RADIUS OF CURVATURE OF CORNEA: radius of curvature as measured at the center portion of the cornea where the center portion has a diameter of 3 mm.

OPTICAL PATH LENGTH (OPL): the integral of the index of refraction (n) times the thickness (t) of each medium along the path of the ray.

DIFFRACTION: the bending of light rays as they pass by an obstruction or through an opening such as the aperture of a lens.

AIRY DISC: the image point of a point source produced by a perfect optical system having a circular aperture. This image has a bright central disc, surrounded by dark rings and light rings of decreasing intensity.

RADIUS OF AIRY DISC: the radius of the first dark ring of the Airy disc.

ROOT MEAN SQUARE (RMS) VALUE: the square root of the average of the squares of a series of related values.

ROOT MEAN SQUARE VALUE OF THE OPTICAL PATH DIFFERENCE (RMS OPD): square root of the average of squares of the OPD values for an appropriate sampling of the rays forming the image of a point source.

SPOT DIAGRAM: shows the locations in the image plane of rays from a point source, as calculated by ray tracing. A perfect optical system would produce only one point of intersection, i.e., all rays imaging at one focal point. For all practical lenses, the spot diagram has a distribution of points.

RMS RADIUS OF THE SPOT DIAGRAM: root mean square of the distance from the center of the spot diagram to each point.

With the above definitions in mind, the present invention involves apparatus and methods for stabilizing the position of the eye during examination and/or treatment. The present invention also reduces aberrations produced by an irregularly shaped cornea. In particular, the present invention may be part of an optical system used for examining interior structures of the eye such as the cornea, iris, crystalline lens, vitreous humor, and retina. The contact lens element preferably has selected dimensions for stabilizing the position of the eye, for reducing aberrations produced by irregularly shaped corneas, and for mounting on an optical instrument, e.g., a microscope.

Referring to the figures, FIG. 1 schematically shows how a rigid contact lens element 10, a liquid 50, and an optical system 100 cooperate to affect light rays 60. The contact lens element 10 and an eye 30 to be examined or treated form a space 40 which is filled with liquid 50. The contact lens element 10 and the liquid 50, as discussed in more detail below, provide an optical link between the eye 30 and the optical system 100. The eye 30 to be examined or treated includes a cornea 32, a limbus 34, a sclera 36, and a crystalline lens 38.

The contact lens element 10 includes a first lens piece 12 including a first lens element 20 and a second lens element 22. As discussed in more detail below, the first lens piece 12 includes a surface 21 that is designed to contact the cornea 32 and is designed to hold liquid 50 against the cornea 32.

The contact lens element 10 further includes a second lens piece 14 including a third lens element 24 and a fourth lens element 26. The second lens piece 14 includes a convex surface 27 which increases the numerical aperture (NA) of the system including the contact lens element 10 and microscope objective 110. As discussed in more detail below, a surface 25 between the third lens element 24 and the fourth lens element 26 is curved to correct chromatic aberrations caused by the convex surface 27.

The optical system 100 includes a microscope objective 110 which, in the illustrated embodiment, includes ten lenses 112, 114, 116, 118, 120, 122, 124, 126, 128, 130. The optical system 100 also includes a tube-length corrector lens 140 which includes two lenses 142, 144. The microscope objective 110 may, for example, have a numerical aperture of 0.40 and a magnification of 20×, such as an Olympus or Nikon long working distance 20× microscope objective.

The combination of the contact lens element 10 and the microscope objective 110 has a relatively high NA. The NA may be about 0.6 to 0.8, more preferably about 0.7 to 0.8 such as about 0.76.

The contact lens element 10 is preferably physically mounted on the microscope objective 110. The contact lens element of the present invention, however, may be hand-held against the cornea, and any viewing instrument may be used to examine the eye by viewing through the contact lens element of the present invention. However, attaching the contact lens element of the present invention to a microscope or fundus camera is desirable so that the contact lens element and the microscope or fundus camera remain in alignment. Thus, physical attachment of the contact lens element 10 and the microscope objective 110 facilitates accurate alignment of the contact lens element 10 with respect to the optical axis of the rest of the optical system of the microscope.

Figure 2:
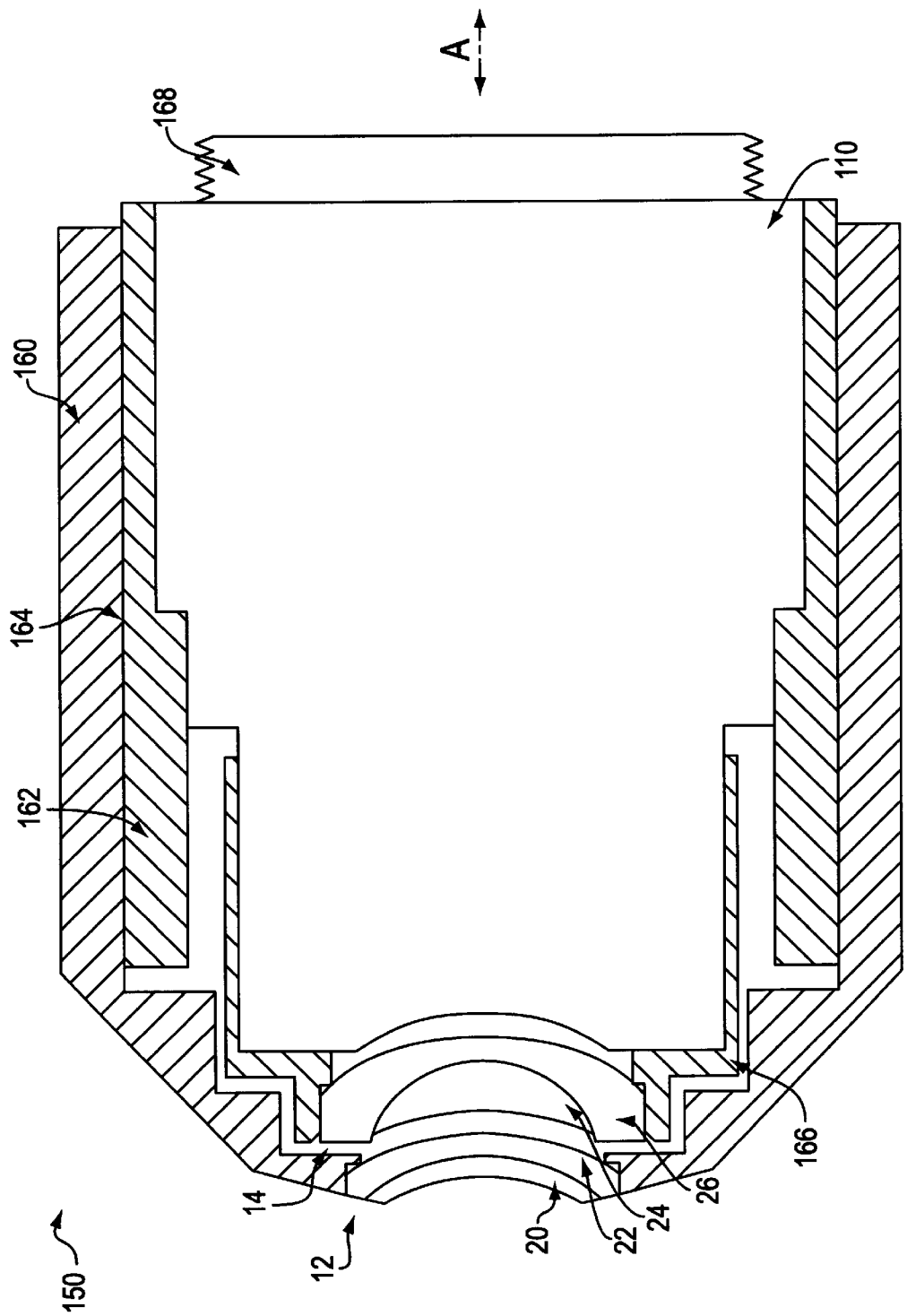
FIG. 2 is a cross-section of another embodiment of the contact lens element according to the present invention in a mount.

FIG. 2 illustrates a mount 150 for mounting and focusing the contact lens element 10. Mounting is important because it facilitates aligning and centering of the optics, including the eye 30.

The mount 150 includes a sleeve bearing mount 160. Within the sleeve bearing mount 160 is an inner bearing mount 162 which is attached to the objective lens 110. The inner bearing mount 162 includes a bearing surface 164 adjacent to the sleeve bearing mount 160. The sleeve bearing 160 is capable of sliding motion as illustrated by each direction of arrow A.

Attached to the microscope objective 110 is a contact element sleeve 166 for holding the second lens piece 14 of the contact lens element 10. The microscope objective 110 is fixed to the microscope body by threaded connection 168. The position of lens 12 may be adjusted by sliding bearing 160 on inner bearing mount 162 in the direction indicated by arrow A.

The purpose of the sliding motion is to adjust the distance between the first lens piece 12 and the second lens piece 14 of the contact lens element 10 to focus the image and to adjust the focal depth. The relative position of the sleeve bearing mount 160 and the inner bearing mount 162 may be adjusted by various adjustment mechanisms (not shown).

Focusing the image and changing the focal depth are accomplished by use of a fine focus mechanism of the microscope. In this regard, the sleeve bearing mount 160 is connected to a fine focus mechanism of the microscope.

Another device and method for mounting a contact lens element on a microscope is found in U.S. Pat. No. 5,359,373 to KOESTER et al., the disclosure of which is incorporated by reference in its entirety. The mount described in this document is useful for contact lens elements which are formed by a single lens piece, e.g., see FIGS. 3–7, as opposed to the contact lens element 10 which involves two lens pieces 12, 14. A difference between the two lens piece contact lens elements and the single lens piece contact elements is that two lens piece contact lens elements facilitate examination and treatment of structure in the eye that are deeper than the cornea.

Figure 3:
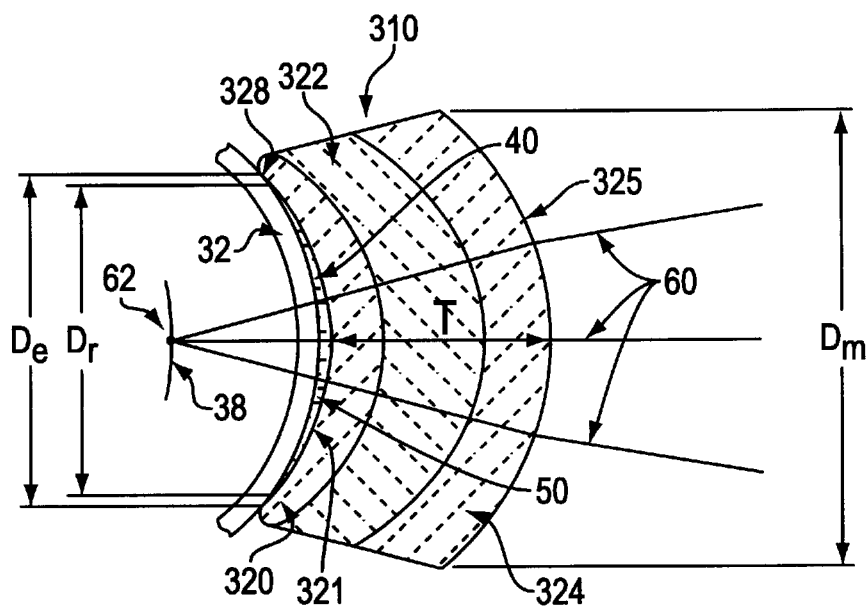
FIG. 3 is a cross-section of a cornea and yet another embodiment of the present invention involving a contact lens element for contacting the cornea along a smoothly polished circular rim.

FIG. 3 illustrates a rigid contact lens element 310 formed by a single lens piece. The contact lens element 310 and other contact lens elements of the present invention may be separate from or part of a microscope objective lens. The contact lens element 310 includes a first lens element 320, a second lens element 322, and a third lens element 324. The contact lens element 310 and the eye 30 form a space 40 which is filled with a liquid 50, which liquid 50 is discussed in more detail below.

The selection of the lens elements 320, 322, and 324, including the thicknesses, radii of curvature, indices of refraction, and indices of dispersion, should be made with a view toward correcting spherical and chromatic aberrations, while still providing an increase in NA for the structure. Increasing the NA increases resolution, increases light gathering power, and reduces the optical section thickness in a confocal microscope. The advantages of higher NA translate into the ability to detect and resolve smaller structures that scatter or reflect light only weakly. The reduced optical section thickness also serves to reduce or to eliminate light from out-of-focus regions that would otherwise obscure subtle details in the image.

The front surface of the contact lens element 310 is designed to facilitate contact with the cornea 32 and to provide a good optical interface. The front surface of the contact lens element 310 is designed to form a space between the contact lens element 310 and the cornea 32 to include a liquid 50.

The front surface of the contact lens element 310 includes a concave contact surface 321 for contacting the cornea 32 and for forming a space between the contact lens element 310 and the cornea 32. The curvature at the center of the contact surface 321 is spherical with a radius of curvature that is less than approximately the radius of the exterior surface of the cornea 32. Thus, the curvature of the contact surface 321 may be less than the radius of the exterior surface of the cornea 32.

As previously noted, corneas are aspheric, i.e., flatter near the edge than in the center. In other words, the radius of curvature of the cornea is shorter in the central portion of the cornea and longer in the peripheral portion of the cornea. The radius of curvature of the cornea, however, is generally considered to be the radius of curvature of the central portion of the cornea having a diameter of 3 mm. Since the contact lens element usually rests on the peripheral portion of the cornea which is flatter than the central portion, the radius of curvature of the contact lens element may be slightly greater than the radius of curvature of the central portion of the cornea without the contact lens element coming into contact with the central portion of the cornea when the contact lens element is in contact with the peripheral portion of the cornea.

Further, a minimal amount of contact between the contact lens element and the central portion of the cornea is also acceptable so long as the contact lens element does not deform the cornea. The contact between the cornea and the contact lens element along the rim allows the cornea to assume its normal shape inside the rim, and the fluid fills the space between the cornea and the concave surface 321.

To optimize the image, the concave surface 321 of the contact lens element 310 may optimally have a radius of curvature which equals the distance to the focal point 62. With such a radius of curvature, light rays 60 will pass through this surface at a right angle so that minimal spherical or chromatic aberrations will be produced by concave surface 321. Such a property is particularly important for detailed examinations or treatments of the eye. Thus, selection of the preferred radius of curvature of the concave surface 321 may depend upon the depth of the structure to be examined or treated.

In view of the above and taking into consideration that the radius of curvature of the central portion of a human cornea is typically about 7.8 mm, the radius of curvature of the central portion of the contact lens element 310 is preferably less than about 8 mm, or more preferably about 5.5 to 7.6 mm. The present invention may also be used to examine non-human eyes in which case the radius of curvature would be changed appropriately. The exact preferred radius of curvature at the center of the contact surface 321 depends on various factors such as the optical design that yields the best image.

In order to obtain an NA substantially greater than that provided by the microscope objective itself, it is desirable that the contact lens element 310 have positive optical power. A convex surface 325 on the rear surface of the contact lens element 310 is selected so as to provide most of the desired power. If the center of curvature of the convex surface 325 is aligned with the image of the structure of the eye that is to be examined or treated, then the aberrations caused by the convex surface 325 will be minimized.

The radius of curvature of the convex surface 325 of the contact lens element 310 depends on the working distance of the objective, the depth of the focal plane, and the specific design of the contact element. In particular, the convex surface 325 of the contact lens element 310 may optimally have a radius of curvature which corresponds to the distance from the surface to the image of the point 62. The image of point 62, as seen from surface 325, is defined as the point from which rays from point 62 appear to come as the rays reach surface 325. With such a radius of curvature, light rays 60 will pass through this surface at a right angle such that aberrations caused by convex surface 325 are minimized.

With the above in mind, the convex surface 325 of the contact lens element 310 may preferably have a radius of curvature of about 5 mm to 15 mm, more preferably about 6 to 12 mm, and most preferably about 7.5 to 10 mm.

Although the contact lens element 310 of FIG. 3 includes three lens elements, the contact lens element of the present invention may include one or more lens elements. If only one lens element is used, the contact lens element does not have the same focus for light of different wavelengths, e.g., red and blue, and chromatic aberrations result. Further, if only one lens element is used, the contact lens element does not have the same focus for light passing through the center of the lens and for light passing through outer portions of the lens, i.e., spherical aberrations in which all light rays do not come to the same focal point.

Accordingly, the contact lens element of the present invention preferably includes more than one lens element to correct for lens aberrations such as chromatic and spherical aberrations. The chromatic and spherical aberrations may be corrected by known techniques involving using more than one lens element that are made of different, transparent materials having substantially different dispersions, i.e., large differences in the rate at which the index of refraction changes with wavelength.

In some cases, such as lenses 322 and 324 in FIG. 3, the difference in index of refraction between adjacent lens elements is essentially zero but the dispersions are chosen to be substantially different. For example, the difference in dispersion between the two lenses could be greater than about 55, such as about 15 to 75, or about 20 to 40, or about 20 to 30. In other designs, the difference in index of refraction between adjacent lens elements with respect to the design wavelength, i.e., the center wavelength of the spectrum of light being utilized (587.6 nm in this case), may be up to about 0.6.

In general, the contact lens element uses as few lens elements as possible to obtain the desired NA, resolution, and flatness of image. In particular, the minimum number of lens elements required increases with increasing NA, resolution, and degree of flatness of the image. Flatness of image is important, e.g., to produce an image on film.

Preferred materials for the one or more lens elements of the contact lens element include glasses such as "SF4", "SF8", and "LaSFN31"available from Schott Glass Technologies, Inc., Duryea, Pa., or plastics such as polymethyl methacrylate (PMMA). In the embodiment shown in FIG. 3, the first lens element 320 is fused silica, the second lens element 322 is a flint glass, e.g., "SFL6" available from Schott Glass Technologies Inc., and the third lens element 324 is a crown glass element, e.g., "BK7" also available from Schott Glass Technologies Inc. Alternatively, the lens 322 could be formed of "LaK 31" glass available from Schott Glass Technologies, Inc., Duryea, Pa., which has an index of refraction of 1.70 and a dispersion of 56.2, and lens 324 could be "SF 15" glass also available from Schott Glass Technologies, which has an index of refraction of 1.70 and a dispersion of 30.

The separate lens elements may be assembled by adhesive bonding through use of optical cements such as Norland Optical Adhesives available from Norland Products Inc., New Brunswick, N.J.

After the number of lens elements and the materials for the lens elements are chosen, a computer software program may be utilized. For example, one may employ an "OSLO PRO" or "OSLO SIX" (Optical System Layout and Optimization) computer software program available from Sinclair Optics, Fairport, N.Y., to aid in selecting the specifications of the first lens element 320, the second lens element 322, and the third lens element 324.

The computer program may be used to perform the following steps. A trial curvature is assigned to the rear surface. The curvature of cemented surfaces are then calculated such that chromatic and spherical aberrations are minimized. The results are then checked to see if the overall power of the lens is satisfactory, and if the resulting image is of sufficient quality. Adjustments are made to the radii of the surfaces to obtain the desired magnification power. Then an optimization program can be utilized to modify the radii of the surfaces and the thicknesses of the components to improve the image quality while holding the power of the lens constant and holding the overall length at the desired value. If the image quality is not yet satisfactory, a new selection of lens element materials can be made and the process is then repeated.

In principle, the above steps are best undertaken when the combination of the contact lens element and microscope objective are analyzed as a unit. However, it may happen that the exact details of the objective are not known. If the objective is known to produce an image that is essentially perfect except for the limitations imposed by the diffraction of light, then the contact lens element can be designed as an independent component.

The contact lens element 310 is designed to touch the cornea 32 along a smoothly polished circular contact rim 328 that is a predetermined radial distance from the center of the contact lens element 310. Thus, the curvature at the central portion of the contact surface 321 is spherical and the curvature near the circular contact rim 328 does not need to be spherical. A smoothly polished contact rim 328 is used because it is undesirable to have a sharp corner contacting the cornea 32. Thus, depending upon how much pressure is placed on the contact lens element 310, the smoothly polished contact rim 328 contacts the cornea 32 over a width, as opposed to forming a line of contact.

The inner diameter ($D_r$) of this contact rim 328 defines the diameter of the volume 40, i.e., the diameter of the border between the liquid 50 and where contact occurs between the eye and the contact lens element 310, as shown in FIG. 3. The diameter ($D_r$) is selected to be greater than the diameter of the bundle of light rays 60 that pass through the cornea 32. Although the actual diameter will depend upon the application, the diameter ($D_r$) of the contact rim 328 may preferably be about 3 to 12 mm, more preferably about 6 to 12 mm, and most preferably about 6 to 10 mm.

Using a circular contact rim 328 for contacting the cornea 32 allows the central portion of the cornea 32 to retain its natural shape and to avoid or minimize any wrinkling in the central region where the imaging rays pass through. Thus, the circular rim 328 helps provide some connection between the cornea 32 and the optical instrument, e.g., the objective lens of a microscope, to help stabilize the axial, i.e., front-to-back, position of the eye during examination. This contact, however, does not prevent the eye from making its normal, involuntary eye motions, such as saccades, slow drifts, or tremors, but it does help to maintain the detail of interest at the focal plane of the optical system.

The diameter ($D_e$) at the end for contacting the eye is preferably slightly greater than the diameter ($D_r$) of the contact rim 328. The diameter ($D_e$) at the end for contacting the eye can be different for various applications. When the central portions of the cornea, the crystalline lens, or the retina are to be examined, the diameter ($D_e$) can be large, e.g., up to about 13 mm. In this regard, the cornea of an adult is about 12 mm in diameter or slightly larger. The rim will then contact the cornea at or near the limbus, the transition zone between the cornea and the sclera. When other portions of the cornea, crystalline lens, iris, or retina are to be examined, a smaller diameter ($D_e$) is preferred so that the end for contacting the eye can be placed against the cornea at locations away from the center. For example, an end with a diameter ($D_e$) of about 6 mm could be placed as far as 3 mm from the center of the cornea and still rest entirely on the cornea.

If the contact surface 321 is positioned so that part of it rests on the sclera, the circular rim 328 will not uniformly contact the surface of the eye 30 because the radii of curvature of the sclera and cornea are different. This poor contact can cause wrinkling of the cornea 32 due to unequal pressure and/or a wedge-shaped space 40 between the contact lens element 310 and the eye 30. Either situation will produce aberrations in the optical system.

Thus, the diameter ($D_e$) of the contact lens element 310 at an end for contacting the eye may preferably be about 4 to 13 mm, more preferably about 7 to 13 mm, and most preferably about 7 to 11 mm. More specifically, the diameter ($D_e$) is preferably about 8 to 13 mm for examining central portions of the eye and about 5 to 9 mm for examining other portions of the eye. These values for the diameter ($D_e$) are based on optical considerations only; experience with subjects and patients will help determine the optimum diameter.

A diameter ($D_m$) of the contact lens element 310 at an opposite end for facing an optical instrument, e.g., microscope, must be large enough that all rays that form the image are transmitted, even after the lens has been mounted. Exact dimensions of the diameter ($D_m$) depend on the NA, objective used, mounting design, etc. For example, the diameter ($D_m$) may preferably be about 13 to 19 mm.

The overall thickness of the contact lens element should be such that when the front surface contacts the cornea, the body of the microscope objective does not touch the eye or the eyelid. Other factors that determine the overall thickness of the contact lens element are the number of lens elements required to obtain the correction needed, the minimum thickness at which each component can be made, and the curvature of each component. Furthermore, the contact lens element should be thin enough that the virtual image it forms is at the focal point of the microscope objective.

Because the contact lens element 310 is preferably used in conjunction with microscopes having a working distance of about 8 to 20 mm, the thickness (T) of the contact lens element 10 at its center is preferably about 4 to 20 mm, more preferably about 6 to 16 mm, and most preferably about 8 to 12 mm.

For embodiments involving a plurality of lens elements, the thickness of the individual lens elements at the center is preferably about 0.5 to 10 mm, more preferably 1 to 8 mm, and most preferably about 1 to 5 mm.

It is well known that a microscope objective of high NA that is designed for a particular thickness of cover glass does not perform well when used with a cover glass of different thickness. This principle holds for the high NA, single piece contact lens elements of the present invention as well. Thus, if the contact lens element is designed to produce a good image for a focal plane that is located, say, 500 microns posterior to the surface of the cornea, the contact lens element may not produce a good image of a plane that is 250 microns posterior to the surface. To study the full 500 microns thickness of the cornea, it may be preferable to have several different contact lens elements. A set of three contact lens elements, each having a different focal range of 200 microns, would suffice.

To obtain such a set of contact lens elements, one approach is to repeat the design procedure for each of the several depths in the cornea. The radii of the spherical surfaces would then be different for each case.

For contact lens elements having a plurality of lens elements, another approach for obtaining a set of contact lens elements having different focal depths is to make the front lens element from a material that has optical properties similar to those of the cornea. Then the front lens element can be fabricated in a different thickness for each desired focal plane in the cornea. The optical surfaces of the other lens elements can remain the same. This procedure reduces the number of different optical components that must be designed and manufactured. The front lens element may be fused silica based on its low refractive index, 1.46, closer to the index of refraction of the cornea (1.376) than most optical glasses. Also, the dispersion of fused silica is low, as is that of the cornea.

The contact surface 321 has a concave shape for a number of reasons. One reason for using a concave shape is that when a flat surface is used to contact the cornea 32, as in applanation tonometry or specular microscopy, the cornea 32 becomes wrinkled. The wrinkles are seen as dark bands across the endothelial cell layer in specular microscopy, and as a mosaic pattern during fluorescein examination following applanation tonometry. Further, when a flat optical surface contacts the cornea 32, the image of the retina seen through the cornea 32 is aberrated, i.e., blurred.

Still further, the concave shape of the contact lens element 310 allows the space or meniscus volume 40 next to the cornea 32 to be filled with liquid 50. The liquid 50 is important because it eliminates or greatly reduces the reflection of light from the corneal surface and the adjacent lens surface. The thickness of the liquid 50 at the center of the contact lens element 310 is preferably about 0 to 20 mm, more preferably about 0 to 5 mm, and most preferably about 0 to 1 mm.

A practical problem of the embodiment of FIG. 3 is how to fill the volume 40 with liquid 50 without trapping air bubbles. In many cases, it is possible to put some, e.g., a drop, of the liquid 50 on the eye. For liquids that are relatively viscous, the liquid 50 will stay in the form of a lump long enough so that a contact lens element may be pressed against the eye such that excess liquid is squeezed out of the volume 40.

Referring to FIG. 1, the space 40 may be filled with liquid 50 from the bottom using a small diameter hypodermic needle 42 attached to a filling tube 44. The diameter of the hypodermic needle 42 depends on the viscosity of the liquid 50 and the size of the contact lens element. For example, the inside diameter of the hypodermic needle may preferably be about 0.25 to 1 mm, and more preferably about 0.5 to 1 mm.

The hypodermic needle 42 is inserted into a small hole 46 through the contact lens element 10, leading from the outside to the bottom of the space 40. The diameter of the hole 46 depends on the viscosity of the liquid 50 and the size of the contact lens element. The diameter of the hole 46 is preferably about 0.25 to 1 mm, and more preferably about 0.5 to 1 mm.

Preferably, the hole 46 enters the space 40 at a convenient angle from the edge of the contact lens element 10. At the top of the space 40 is a small hole 48 in the contact lens element 10 that serves as a vent. The diameter of the hole 48 is preferably about 0.25 to 1 mm, and more preferably about 0.5 to 1 mm.

For a subject or patient whose cornea 32 is free from irregularities such as astigmatism, the index of refraction of the liquid 50 is not critical. In this case, the subject's tears will normally be satisfactory. Alternatively, artificial tears may be used. Examples of artificial tears include "Hypo Tears" (having an index of refraction of 1.3405) available from CIBA Vision Opthalmics of Atlanta, Ga. and "Bion Tears" available from Alcon, Fort Worth, Tex.

Many corneas 32, however, have a surface that exhibits astigmatism, i.e., greater curvature in one azimuthal direction than in the perpendicular direction. Further, almost all corneas, when measured carefully, have some degree of irregular astigmatism in which the variations in curvature are not correctable by the usual toric surfaces that are used in spectacle lenses.

While corneal aberrations can be sufficiently compensated for the purpose of vision correction, they need to be eliminated more completely for microscopic examination of eye structures. The high numerical aperture needed for high resolution microscopy requires that the bundle of imaging rays must pass through a larger portion of the cornea than is normally utilized for visual tasks. The aberrations that are introduced into the image forming bundle of rays generally increase in magnitude with increasing aperture size. Accordingly, for an optical instrument designed to form images of interior structures of the eye, astigmatism will cause the image to be degraded.

For corneas which exhibit astigmatism, these images can be improved if the space between the contact lens element 310 and cornea 32 is filled with a liquid 50 having a refractive index equal to or close to the 1.376 refractive index of the cornea 32. When the refractive indices of the liquid 50 and the cornea 32 are exactly equal, then the irregular shape of the corneal surface has no aberrating effect on the light passing through this interface. With such a liquid, the monochromatic aberrations due to the exterior surface of the cornea 32 can in principle be totally eliminated, since there would be no refraction of light at the corneal surface such that no monochromatic aberrations are introduced at the irregular corneal surface.

The index of refraction of liquid 50, which is preferably optically clear, may be greater than 1.337 and should preferably be about 1.337 to 1.415, more preferably about 1.366 to 1.386, and most preferably about 1.370 to 1.382. Any index of refraction between about 1.337 and 1.415 would provide some improvement over the use of the tear layer.

Further, any index between 1.366 and 1.386 would minimize the aberrating effect of an irregular cornea and would not introduce aberrating effects of its own. For instance, if the index of refraction can be raised to about 1.372, then the aberrations of the cornea can be reduced to about 1% of that for the cornea in air.

The liquids, of course, must be clear, homogeneous, e.g., free of bubbles, bio-compatible, safe, and comfortable for application to the eye. Examples of liquids that have an index of refraction greater than that of tears include 40 wt % dextrose aqueous solution (also known as glucose gel, and which has a refractive index of 1.42) such as "Glutose 45" available from Paddock Laboratories Inc., Minneapolis, Minn, and 15 wt % gelatin aqueous solution (having an index of refraction of 1.363), dry gelatin being available from Knox Gelatine Inc., Englewood Cliffs, N.J.

To obtain the ideal index of refraction, the index of refraction of the liquid may be adjusted. One method of adjusting the index of refraction of the liquid is to increase or decrease the concentration of biocompatible solutes. Biocompatible solutes include salts such as sodium chloride, sugars such as dextrose, sucrose, glucose and maltose, and proteins such as albumin and gelatin. For instance, a protein such as albumin may be added to sterile water to adjust the index of refraction. Based on data from the Handbook of Physics and Chemistry, liquids which should have a refractive index of about 1.376 include 16 wt % aqueous dextrose solution, 27 wt % aqueous sucrose solution, and 28 wt % aqueous maltose solution.

Concerning the selection of the liquid, if the cornea were thin and had the same shape on the anterior and posterior surfaces, then it could be argued that the best index for the liquid would be the same as the index on the posterior side of the cornea, which is approximately 1.336. Coincidentally, this refractive index of 1.336 is the same as the index of the tear layer, therefore the tear layer would be an ideal liquid for eliminating aberrations produced by the cornea. Unfortunately, the shape of the posterior corneal surface is not known very accurately, since it has not been mapped with the same precision as the anterior surface. However, it is known that the cornea is generally thicker toward the periphery than at the center. For this reason alone it is not safe to assume that the posterior surface has the same shape as the anterior surface. In other words, if the cornea were thin enough it would not refract light but the cornea is actually thick enough to refract light. Therefore, the best strategy for a cornea with an irregular anterior surface is to choose a contact liquid whose index of refraction matches that of the anterior of the cornea as closely as possible.

Figure 4:
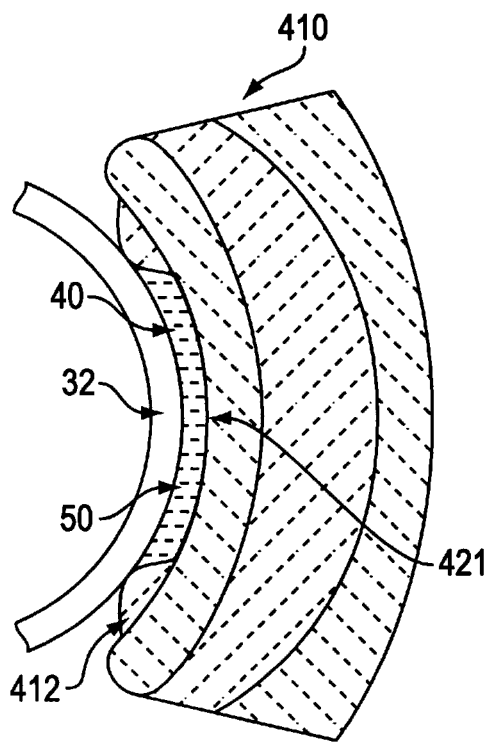
FIG. 4 is a cross-section of a cornea and still another embodiment of the present invention involving a contact lens element which includes a polished circular ring for contacting the cornea.

FIG. 4 illustrates another embodiment involving a polished circular contact ring 412 that contacts the cornea 32. The circular contact ring 412 is attached to a lens 410. The contact ring 412 can be made of plastic, such as polymethyl methacrylate (PMMA) which can be fabricated by single point diamond machining. The lens 410 and the circular contact ring 412 may be made of the same or different materials. The lens 410 may be made of any of the materials used for lens 310.

The contact ring 412 is preferably formed as a separate piece and then adhesively bonded to the lens 410 using an adhesives such as an epoxy cement or optical adhesive such as Norland Optical Adhesives, discussed above. Alternatively, the contact ring and the lens could be machined from one piece by using a machining technique such as single point diamond machining. Still another alternative is to mold the lens and the contact ring as one piece.

The height, i.e., axial thickness, of the circular contact ring is preferably about 0.5 to 3 mm. The width, i.e., radial thickness, of the circular contact ring is preferably about 1 to 5 mm. The inner diameter of the circular contact ring is preferably about 6 to 13 mm.

In this embodiment of FIG. 4, the radius of curvature of the lens 410 could be less than, greater than, or the same as that of the cornea 32, so long as it provides a volume between the cornea 32 and a distal surface 421 of the lens 410 for the index-selected liquid 50. The value of this approach is that the radius of curvature of the distal surface 421 is no longer constrained to be less than that of the cornea 32. Therefore, the radius of this surface 421 can be varied, within limits, in the design of the imaging optics to obtain the best possible image quality. In fact, the distal surface 421 could be concave.

Figure 5:
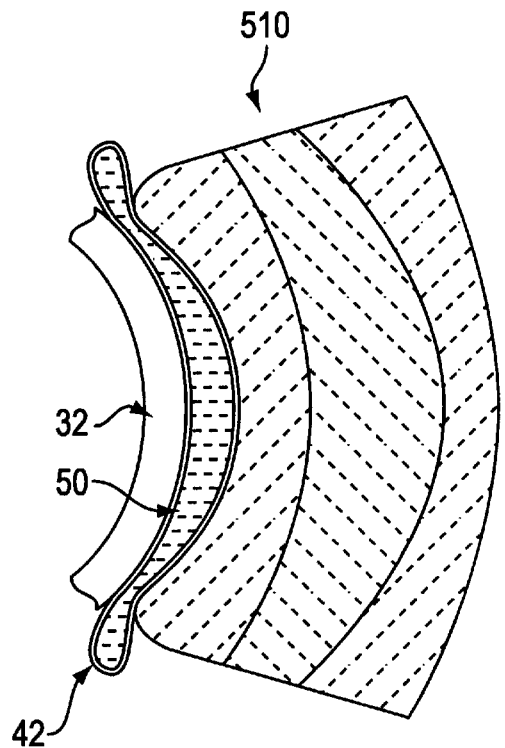
FIG. 5 is a cross-section of a cornea and still another embodiment of the present invention involving a contact lens element for holding a transparent bag holding a liquid against the cornea.

FIG. 5 shows yet another embodiment involving a bag 42 for holding liquid 50. If a liquid has the desired index of refraction but has a viscosity that is too low to stay in the meniscus chamber 40 of the embodiments shown in FIGS. 1–4, the liquid can be contained in a chamber of bag 42. The preferred size of the bag 42 is about 8 to 15 mm in diameter. The wall thickness of the bag 42 is preferably about 0.02 to 0.3 mm.

Bag 42 may be a flexible transparent plastic, such as "SARAN" resin available from Dow Chemical, Midland, Mich., clear polyethylene available from DuPont, Wilmington, Del., or thin latex. Of course, the optical quality of the bag material must meet the standards of optical path difference that apply to the cornea/liquid interface.

The contact lens element 510 may be similar to the contact lens elements of FIGS. 1–4. The design of the contact lens element 510, however, should take into consideration the thickness of the bag 42 and the liquid 50. For instance, the wall thickness of the bag 42 as well as the thickness of the liquid 50 will affect the focal depth of the contact lens element 510.

Figure 6:
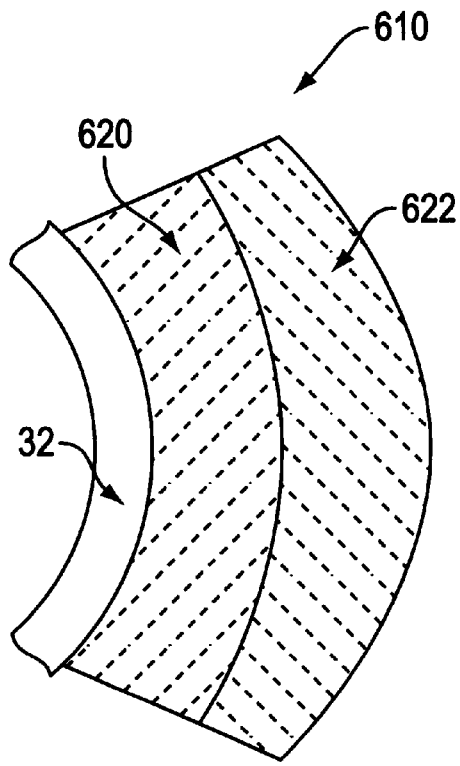
FIG. 6 is a cross-section of a cornea and still another embodiment of the present invention involving a contact lens element made of a soft material.

FIG. 6 illustrates another embodiment involving a contact lens element 610 which includes a contact 620 that is made of a soft material such as high water content hydrogels such as a contact lens with high water content. Of course, the material should be transparent and homogeneous. The contact 620 must be soft enough to conform to the shape of the eye without distorting the shape of the eye. The contact 620 preferably has a concave contour similar to the embodiment shown in FIG. 3, and is supported by a substrate 622 which may, for example, be made of any of the glasses or plastics which are useful as the contact lens element as described above. Further, to facilitate optical continuity, the material should also be able to form an optical contact with the substrate 622. The contact lens element 610 could be disposable to reduce the possibility of cross-contamination.

Figure 7:
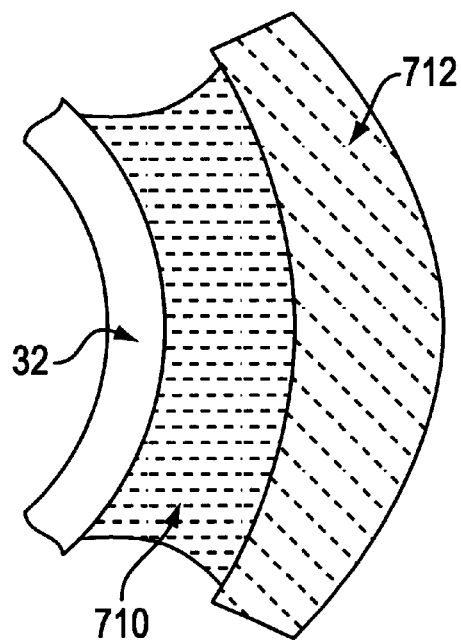
FIG. 7 is a cross-section of a cornea and still another embodiment of the present invention involving a malleable material attached to a microscope lens.

FIG. 7 illustrates yet another embodiment of the present invention involving a transparent, optically homogeneous, biocompatible material 710 with a refractive index of preferably about 1.337 to 1.415, more preferably about 1.366 to 1.386, and most preferably about 1.370 to 1.382. The material 710 is cohesive or attachable to the front lens 712 of an optical microscope and is soft or malleable enough to conform to the shape of a cornea 32 without significantly distorting the shape of the cornea 32. The material 710 preferably has a viscosity such that the material deforms to conform to the shape of the cornea without changing the shape of the cornea. Since the normal pressure in the eye is about 19 mm Hg, the material 710 should not exert a pressure equal to or more than this when it has been deformed to the shape of the cornea. The material 710 should preferably be viscoelastic.

Examples of material 710 which is preferably a jelly-like material include sodium hyaluronate, e.g., "Healon" available from Pharmacia Upjohn, Kalamazoo, Mich., methylcellulose solution, e.g., "Goniosol" available from Iolab Pharmaceuticals, Claremont, Calif. Although these materials have refractive indices of about 1.336 or 1.337, the refractive indices of these materials may preferably be modified by adding suitable solutes such as proteins, salts, or sugars, as discussed above.

Figure 8:
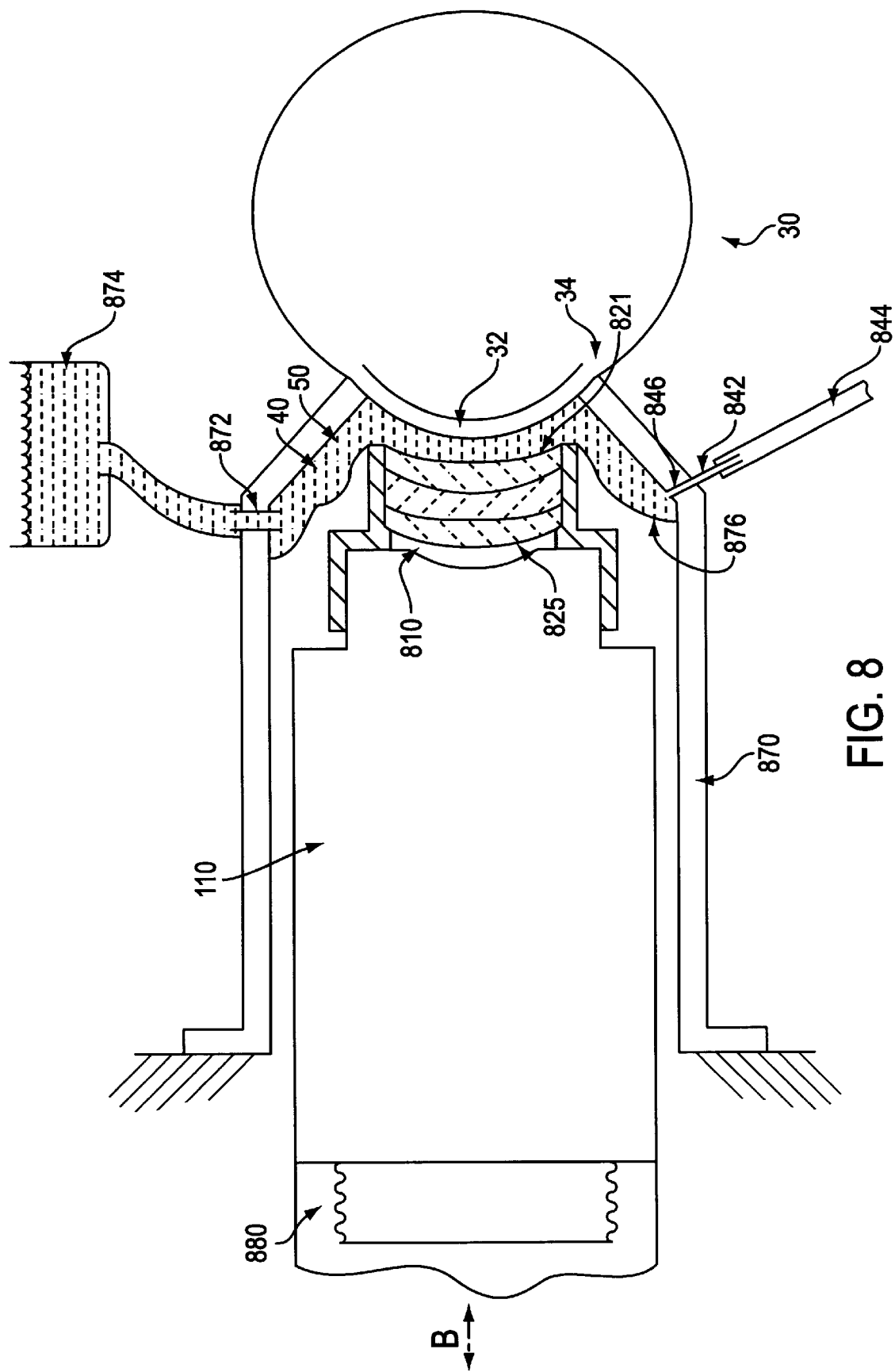
FIG. 8 is a cross-section of a cornea and another embodiment of the present invention involving a hollow tube for contacting the cornea.

FIG. 8 illustrates another embodiment of the present invention involving a hollow tube 870. In this embodiment, the contact with the cornea 32 is not made by a lens element 810. Instead, contact with the cornea 32 is made by the hollow tube 870 which is a watertight material such as stainless steel. In particular, the hollow tube 870 includes an end which is shaped to contact the cornea 32 at or near the limbus 34. The hollow tube 870 is stationary and, therefore, serves to stabilize the eye 30.

A liquid 50 is provided in a space 40 between the cornea 32 and the lens 810. To hold the liquid 50 against the cornea 32, the hollow tube 870 is also provided with a bellows 876 which is made of a watertight, flexible material such as a rubber. The space 40 may be filled with liquid 50 from the bottom using a small diameter hypodermic needle 842 attached to a filling tube 844. The diameter of the hypodermic needle 842 depends on the viscosity of the liquid 50. For example, the inside diameter of the hypodermic needle 842 may preferably be about 0.25 to 1 mm, and more preferably about 0.5 to 1 mm.

The hypodermic needle 842 is inserted into a small hole 846 through the hollow tube 870, leading from the outside to the bottom of the space 40. The diameter of the hole 846 depends on the viscosity of the liquid 50. The diameter of the hole 846 is preferably about 0.25 to 1 mm, and more preferably about 0.5 to 1 mm. At the top of the space 40 is an outlet 872 connected to a reservoir 874. The diameter of the outlet 872 also depends on the viscosity of the liquid and is preferably about 0.25 to 1 mm, and more preferably about 0.5 mm to 1 mm.

To focus an image, the longitudinal position of the lens 810 and microscope objective 110 is variable by use of a fine focus mechanism 880, as shown by both directions of arrow B. As a result, the amount and thickness of liquid 50 between the lens 810 and the cornea 32 is varied. For example, when the microscope objective 110 and the lens 810 are adjusted to the right as shown in FIG. 8, the liquid 50 layer will be made thinner and the excess liquid 50 will be expressed through outlet 872 and stored in reservoir 874.

The optical system illustrated in FIG. 8 includes the microscope objective 110 and the lens 810 which includes a single lens piece and the spacing between the microscope objective 110 and the lens 810 remains constant. Therefore, the design process is somewhat simpler in that the aberration corrections are for one configuration only. Further, since the lens 810 does not normally contact the cornea 32, a front surface 821 of the lens 810 does not need to be designed to fit the cornea 810 and may be concave, flat, or convex. Because of the chromatic and spherical aberrations caused by convex surface 825, the lens 810 preferably includes a plurality of lens elements to correct theses aberrations, as discussed above. The lens 810 may be fixed to the microscope objective 110 or may be a part of the objective lens for those objective lenses that are designed to be immersed in water. An example of such a water immersion objective is "MSPlan Achromat", 150X, NA 1.25, water, available from Olympus Corporation, Lake Success, N.Y.

The procedure for using the embodiment of FIG. 8 involves anesthetizing the eye 30 to be examined or treated, locating the patient in a chin/head rest, contacting the cornea 32 with the tube 870, injecting liquid 50 into the space 40, focusing the image to examine or treat the eye 30, and then draining the fluid 50 through the hypodermic needle 842 upon completion of the examination or treatment. To inject liquid 50 into the space 40, pressure is applied to the hypodermic needle 842. As the liquid 50 fills the space 40, air is allowed to escape through outlet 872.

With the above embodiments in mind, the present invention may be used with optical instruments that utilize larger regions of the cornea than are used in the contact lens for vision correction applications, where the pupil diameter is usually 3 mm or less and the portion of the cornea being utilized is also about 3 mm in diameter. In order to examine the crystalline lens, the iris, or the retina, the examining instrument may utilize a larger region of the cornea, up to about 8 mm diameter. In this regard, the diameter of the cornea being used depends on the desired NA such that the larger the diameter the better. To form a good image, i.e., an image free from aberrations and blur, the rays passing through the contact lens element, immersion medium, and cornea must have the same optical path length (OPL). OPL is defined as the integral of the index of refraction (n) times the thickness (t) of each medium along the path of the ray. Under normal conditions, a cornea with astigmatism or other irregularity that introduces more than one quarter of a wavelength of optical path length in one ray relative to the other rays in the image forming bundle will cause a degradation in the image. However, if the cornea is immersed in a liquid with a refractive index exactly equal to that of the cornea, then these surface irregularities do not cause a change in the optical path and therefore do not degrade the image.

There may be other sources of astigmatism or optical irregularity that will cause image degradation. The crystalline lens is known to exhibit astigmatism in some people, due probably to both surface and internal irregularities. Some irregularities must also be expected from the posterior surface of the cornea. These sources of aberration cannot be removed by the present invention. Fortunately, in most subjects they are smaller in magnitude than the aberrations produced by the anterior surface of the cornea in air, so that significant benefit can be achieved by eliminating or greatly reducing the aberrating effects of the anterior corneal surface.

The present invention is also directed to various processes. For instance, the contact lens element of the present invention may be used with diagnostic instruments for examining the crystalline lens, including the epithelial cells, fiber cells, suture line structures, and early indications of cataract formation such as microscopic opacification. Such diagnostic instruments include biomicroscopes (also known as a slit lamp), fundus cameras, and scanning laser ophthalmoscopes. Similarly, the contact lens element of the present invention may be used with diagnostic instruments for examining the iris for the presence of inflammatory cells or changes due to disease or trauma.

Further, the present invention may be used with diagnostic instruments for examining the retina with greater resolution than is possible with present ophthalmoscopes, fundus cameras, scanning laser ophthalmoscopes, and slit lamp biomicroscopes. The greater resolution obtained by the present invention is made possible by reducing or eliminating the optical aberrations induced by the cornea when the cornea is in air.

Still further, the present invention may be used with therapeutic instruments such as laser photocoagulators or photodisrupters. These instruments typically utilize a slit lamp biomicroscope to locate the area to be treated by the laser, and the laser beam is directed through a portion of the same optical system to the target. Instruments with higher magnification and the greater resolution provided by the present invention may be able to treat smaller lesions, smaller blood vessels, and lesions that are very close to sensitive areas such as the fovea centralis.

Even further, the present invention may be used in conjunction with systems employing adaptive optics to improve images of internal eye structures. Adaptive optics refers to the field of optical systems that can sense the aberrations or other distortions caused by inhomogeneous media such as the atmosphere or the transparent media in the eye, and can then change the shape of a mirror or other optical element in the system so as to correct the aberrations caused by the media. The result is an image of improved quality. One advantage of the present invention involves the stabilization of the eye of the patient or subject while the adaptive optics are being optimized. The contact with the cornea will not prevent all types of eye motion, such as saccades, but it greatly reduces the axial variation in eye position. Because the contact lens element of the present invention greatly reduces aberrations from corneal astigmatism, the amount of correction required of the adaptive optics is reduced.

Figure 9:
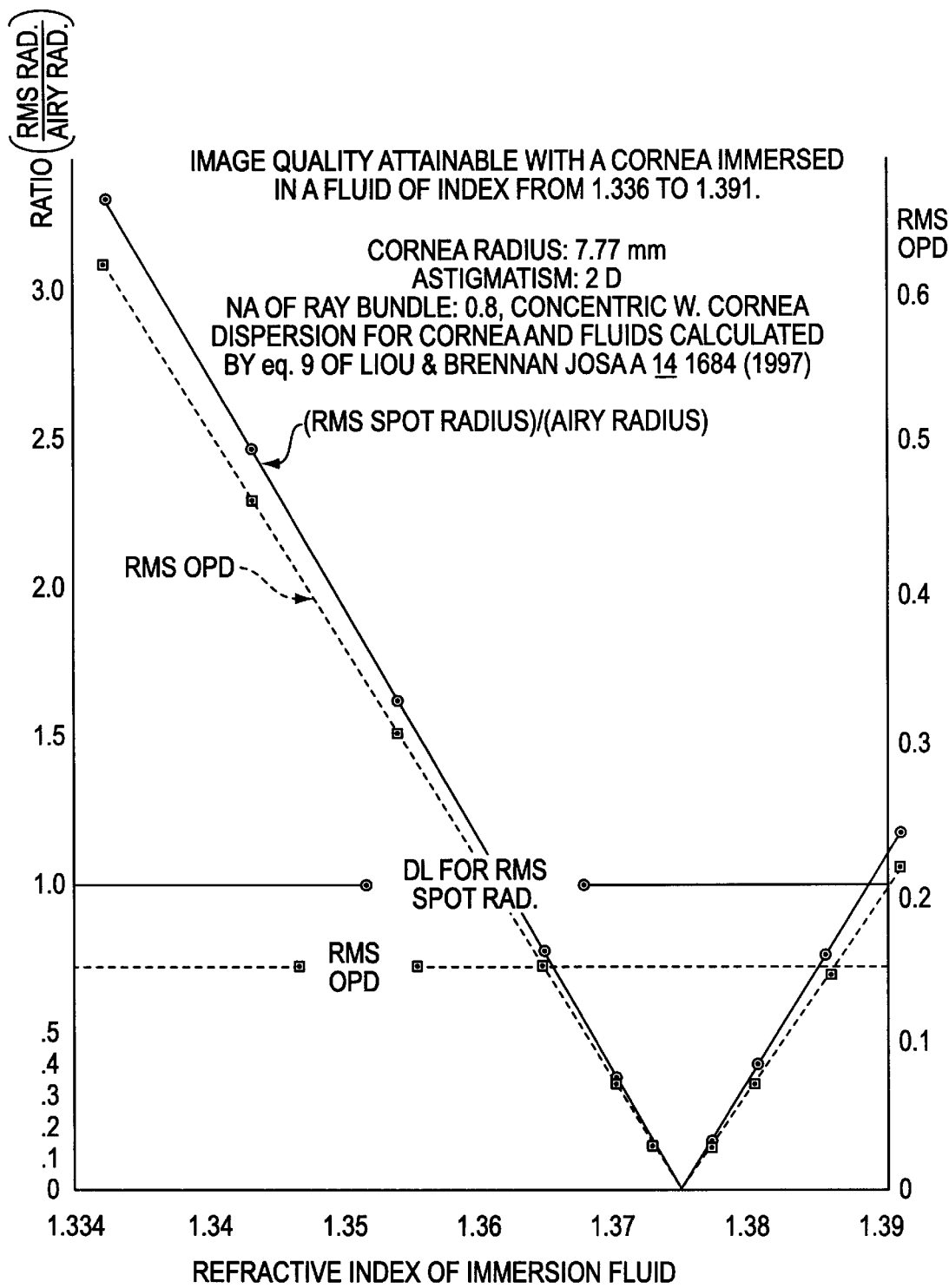
FIG. 9 is a graph illustrating the results of a computer-simulation which show the benefits of the present invention.

FIG. 9 illustrates the results of a computer-simulation which show the magnitude of the benefit that is potentially realized by immersing the cornea in a liquid of predetermined index of refraction. In order to evaluate the aberrating effect of the anterior corneal surface, independent of the posterior corneal surface and the crystalline lens, the quality of the optical wavefront was evaluated after passing through the anterior corneal surface only. To simulate a normal but aberrated cornea, the anterior surface was assumed to be toroidal, with a radius of 7.77 mm in one meridian and a radius of 8.10 mm in the orthogonal meridian, which corresponds to an astigmatism of 2.0 diopters, and the entrance pupil was assumed to be 7.0 mm.

The image quality was evaluated using two criteria: (1) the root mean square (RMS) value of the optical path difference across the wavefront; and (2) the RMS radius of the spot diagram for rays traced from a point source to the image plane, using three wavelengths (486.1 nm, 587.6 nm, and 656.3 nm). It is known that RMS spot radius and RMS OPD values are two measures of aberrations in the optical system. The RMS spot radius includes calculations on all three wavelengths, but not on the effects of diffraction. The RMS OPD includes diffraction effects, but only at one wavelength. When the RMS spot radius is less than the Airy radius and the RMS OPD is less than 0.075 times the central wavelength, then the image should be effectively diffraction limited.

Optical design software ("OSLO PRO" available from Sinclair Optics, Inc., Fairport, N.Y.) was used to analyze the performance of the cornea surface alone. The object point was at the center of curvature of the corneal surface, so that rays were incident at or near normal incidence. This roughly simulates the optical configuration when the posterior crystalline lens is to be examined. The bundle of rays had an included angle of 72 degrees, which corresponds to a numerical aperture (NA) of:

$NA=(n)(\sin \Phi)=(1.376)(\sin 36°)=0.81$.

FIG. 9 presents the results of this analysis. The solid line indicates the change in RMS spot radius as the index of the immersion liquid is varied from 1.336 (the tear layer) to 1.391. The dashed line gives the RMS OPD values. Horizontal lines indicate the upper limits of diffraction limited image quality, i.e., RMS spot radius=Airy disc diameter and RMS OPD=0.075 (the Marechal criterion).

Although FIG. 9 is based on an assumption of 2 diopters of astigmatism, other computer simulations have shown that for corneas with less than 2 diopters of astigmatism the allowed variation of index of refraction increased. Also, an optical system that utilizes a smaller diameter of the cornea could obtain diffraction limited performance with an immersion liquid having an index somewhat less than 1.376. Thus, there would be some value in utilizing immersion liquids with indices between that of tears (1.336) and the value 1.376 listed above. With a 3 mm pupil diameter and 2 diopters of astigmatism, the limiting value for the index was calculated to be 1.340.

FIG. 9 also illustrates that liquids with indices of refraction between 1.376 and 1.386 will yield diffraction limited performance with a cornea having 2 diopters of astigmatism or less. Some improvement relative to natural tears can also be realized with indices greater than 1.386, up to an index of about 1.415 (=1.376+0.039).

While the invention has been described in connection with certain preferred embodiments so that aspects thereof may be more fully understood and appreciated, it is not intended to limit the invention to these particular embodiments. On the contrary, it is intended to cover all alternatives, modifications and equivalents as may be included within the scope of the invention as defined by the appended claims.

What is claimed is:

1. A multi-layered contact lens element for at least one of examination and treatment of ocular tissues, comprising a plurality of lens elements in layers including a first lens element having a recess capable of forming a substantially enclosed space with a cornea of an eye to be examined or treated, the substantially enclosed space being capable of being filled with a liquid, the recess being capable of allowing a central portion of the cornea to be in its natural shape when a peripheral portion of the contact lens element is in contact with a peripheral portion of the cornea.

2. The contact lens element of claim 1, wherein the recess comprises a concave surface having a radius of curvature of about 5.5 to 7.6 mm.

3. The contact lens element of claim 1, wherein the contact lens element includes a hole therethrough for injecting a liquid into a space between the contact lens element and the cornea when the contact lens element is in contact with the cornea.

4. The contact lens element of claim 3, wherein the contact lens element includes a vent.

5. The contact lens element of claim 1, wherein the plurality of lens elements further comprises:
 a second lens element attached to the first lens element; and
 a third lens element attached to the second lens element, the third lens element having an exterior convex surface.

6. The contact lens element of claim 1, wherein the contact lens element comprises at least one material selected from the group consisting of glass and plastic.

7. The contact lens element of claim 1, wherein the first lens element comprises a rim which is capable of contacting the cornea, wherein the rim comprises a protruding contact ring which protrudes from a concave surface which forms a portion of the recess.

8. The contact lens element of claim 1, wherein the contact lens element comprises a plurality of separate pieces.

9. The contact lens element of claim 1, wherein the contact lens element comprises a microscope objective.

10. A contact lens element for at least one of examination and treatment of ocular tissues, comprising a concave surface capable of contacting a cornea of an eye to be examined or treated having a radius of curvature that is less than approximately a radius of curvature of the cornea and having a diameter of about 7 to 12 mm, and an exterior convex surface having a diameter of about 13 to 19 mm, the contact lens element having a thickness of about 8 to 20 mm, wherein the contact lens element includes a hole therethrough for injecting a liquid into a space between the contact lens element and the cornea when the contact lens element is in contact with the cornea, and wherein the contact lens element includes a vent.

11. The contact lens element of claim 10, wherein the concave surface has a radius of curvature less than about 8 mm.

12. The contact lens element of claim 10, wherein the contact lens element comprises a plurality of lens elements.

13. The contact lens element of claim 12, wherein the plurality of lens elements comprises:
 a first lens element forming the concave surface;
 a second lens element attached to the first lens element; and
 a third lens element attached to the second lens element, the third lens element forming the exterior convex surface.

14. The contact lens element of claim 10, wherein the contact lens element comprises at least one material selected from the group consisting of glass and plastic.

15. The contact lens element of claim 10, wherein the contact lens element comprises a rim which is capable of contacting the cornea.

16. The contact lens element of claim 10, wherein the contact lens element comprises a plurality of separate pieces.

17. A contact lens element for at least one of examination and treatment of ocular tissues, comprising a lens including a contact surface and an exterior convex surface, the contact surface comprising a protruding contact ring which forms a recess which is capable of forming a substantially enclosed space with a cornea of an eye to be examined or treated when the protruding contact ring is in contact with the cornea, the substantially enclosed space being capable of being filled with a liquid and wherein the protruding contact ring protrudes from a concave surface which forms a portion of the recess.

18. The contact lens element of claim 17, wherein the lens comprises at least one material selected from the group consisting of plastic and glass.

19. The contact lens element of claim 17, wherein the recess comprises a concave surface.

20. The contact lens element of claim 17, wherein the contact lens element comprises a plurality of lens elements.

21. The contact lens element of claim 17, wherein the contact lens element comprises a microscope objective.

22. A system for at least one of examination and treatment of ocular tissues, comprising:
 an optically clear liquid having a refractive index greater than 1.338; and
 a contact lens element capable of forming a substantially enclosed space with a cornea of an eye to be examined or treated, the substantially enclosed space being capable of being filled with a liquid, and wherein the contact lens element comprises a rounded surface which is capable of contacting a cornea without distorting a shape of the cornea inside of a contact ring region.

23. The system of claim 22, wherein the liquid has a refractive index of about 1.366 to 1.386.

24. The system of claim 22, wherein the liquid comprises an aqueous solution.

25. The system of claim 24, wherein the aqueous solution comprises a salt solution.

26. The system of claim 24, wherein the aqueous solution comprises an organic solution.

27. The system of claim 26, wherein the organic solution comprises at least one protein selected from the group consisting of albumin and gelatin.

28. The system of claim 24, wherein the aqueous solution comprises a sugar solution.

29. The system of claim 22, wherein the contact lens element includes a circular rim which is capable of contacting the cornea.

30. The system of claim 22, wherein the contact lens element comprises a surface having a radius of curvature of about 5.5 to 7.6 mm.

31. The system of claim 22, wherein the contact lens element comprises a plurality of separate pieces.

32. The system of claim 22, wherein the contact lens element comprises a part of an imaging system for examining structures within an eye.

33. The system of claim 32, wherein the imaging system comprises a microscope.

34. The system of claim 32, wherein the contact lens element is rigidly attached to and aligned with the imaging system.

35. The system of claim 22, wherein the contact lens element comprises a microscope objective.

36. The system of claim 22, wherein the contact lens element comprises a hole for allowing the liquid to be injected into a space between the contact lens element and the cornea, and a vent for allowing at least one of air and excess liquid to escape.

37. A system for at least one of examination and treatment of ocular tissues, comprising:
 a liquid;
 a contact lens element having a recess capable of forming a substantially enclosed space with a cornea of an eye to be examined or treated, the substantially enclosed space being capable of being filled with the liquid, the recess being capable of allowing a central portion of the cornea to be in its natural shape when a peripheral portion of the contact lens element is in contact with a peripheral portion of the cornea; and
 a microscope connected to the contact lens element.

38. The system of claim 37, wherein the liquid has a refractive index of about 1.366 to 1.386.

39. The system of claim 37, wherein the liquid comprises an aqueous solution.

40. The system of claim 39, wherein the aqueous solution comprises a salt solution.

41. The system of claim 39, wherein the aqueous solution comprises an organic solution.

42. The system of claim 41, wherein the organic solution comprises at least one protein selected from the group consisting of albumin and gelatin.

43. The system of claim 39, wherein the aqueous solution comprises a sugar solution.

44. The system of claim 37, wherein the recess of the contact lens element comprises a concave surface having a radius of curvature that is less than approximately a radius of curvature of the cornea.

45. The system of claim 37, wherein the contact lens element includes a hole therethrough for injecting the liquid into a space between the contact lens element and the cornea when the contact lens element is in contact with the cornea.

46. The system of claim 45, wherein the contact lens element forms a vent.

47. The system of claim 37, wherein the contact lens element comprises a plurality of lens elements.

48. The system of claim 47, wherein the plurality of lens elements comprises:
 a first lens element capable of contacting the cornea;
 a second lens element attached to the first lens element; and
 a third lens element attached to the second lens element.

49. The system of claim 48, wherein the first lens element comprises the recess which comprises a concave surface with a radius of curvature that is less than approximately a radius of curvature of the cornea.

50. The system of claim 37, wherein the contact lens element comprises a rim which is capable of contacting the cornea.

51. The system of claim 37, wherein the contact lens element comprises a contact surface having a protruding contact ring which is capable of contacting the cornea.

52. The system of claim 51, wherein the contact lens element has a radius of curvature which is sufficient to provide a volume for the liquid between the contact lens element and the cornea when the protruding contact ring is in contact with the cornea.

53. The system of claim 37, wherein the contact lens element comprises at least one material selected from the group consisting of plastic and glass.

54. The system of claim 37, further comprising a bag containing the liquid.

55. A system for examining ocular tissue, comprising:
 a microscope having at least one lens comprising an external lens; and
 a transparent, malleable material attached to the external lens of the microscope, the malleable material being capable of contacting and conforming to a cornea of an eye to be examined or treated, without significantly distorting a shape of the cornea.

56. The system of claim 55, wherein the malleable material comprises an optically homogeneous, biocompatible substance which has a refractive index of about 1.366 to 1.386.

57. The system of claim 55, wherein the malleable material comprises at least one material selected from the group consisting of sodium hyaluronate and methylcellulose solution.

58. The system of claim 55, wherein the malleable material comprises a resilient material having a concave surface for contacting the cornea.

59. The system of claim 58, wherein the resilient material comprises a contact lens comprising water.

60. The system of claim 58, wherein the resilient material is connected to the external lens of the microscope via a substrate.

61. The system of claim 60, wherein the substrate comprises at least one material selected from the group consisting of plastic and glass.

62. A system for at least one of examination and treatment of ocular tissues, comprising:

a microscope objective;

a lens associated with the microscope objective;

a hollow tube including an open end adapted to contact a cornea of an eye to be examined or treated;

an adjustable chamber at the open end of the hollow tube, the adjustable chamber being defined by a movable wall member, a portion of the hollow tube, and an opening forming the open end of the hollow tube, the lens comprising a portion of the movable wall; and at least one aperture associated with the adjustable chamber for introducing a variable volume of liquid into the adjustable chamber when the opening is placed against the cornea.

63. The system of claim 62, wherein the lens is connected to the microscope objective.

64. The system of claim 62, wherein the lens forms a part of the microscope objective.

65. The system of claim 62, further comprising a fine focus mechanism capable of adjusting a position of the microscope objective relative to the cornea.

66. The system of claim 62, further comprising a reservoir associated with the at least one aperture.

67. A method for at least one of examining and treating ocular tissue, comprising:

providing a contact lens element associated with a microscope, the contact lens element having a recessed surface;

contacting the contact lens element with a cornea to form a substantially enclosed space between the recessed surface of the contact lens element and the cornea while allowing a central portion of the cornea to be in its natural shape when a peripheral portion of the contact lens element is in contact with a peripheral portion of the cornea;

at least one of filling the substantially enclosed space with liquid and allowing the substantially enclosed space to become filled with liquid; and at least one of examining and treating ocular tissue by light transmission through the liquid and the contact lens element.

68. The method of claim 67, wherein the recessed surface comprises a concave surface having a radius of curvature that is less than approximately a radius of curvature of the cornea.

69. The method of claim 67, wherein the contact lens element is circular, and wherein the contact lens element is placed on the cornea concentric with a region of the ocular tissue to be examined or treated.

70. The method of claim 67, wherein the substantially enclosed space forms a meniscus.

71. The method of claim 67, wherein the at least one of filling the substantially enclosed space with liquid and allowing the substantially enclosed space to become filled with liquid comprises filling the substantially enclosed space with liquid by using a hypodermic needle that is inserted into a hole in the contact lens element which leads from an outside to the substantially enclosed space, and wherein the contact lens element includes a vent.

72. The method of claim 67, wherein the at least one of examining and treating of the ocular tissue comprises examining a crystalline lens.

73. The method of claim 67, wherein the at least one of examining and treating of the ocular tissue comprises examining an iris.

74. The method of claim 67, wherein the at least one of examining and treating of the ocular tissue comprises examining a retina.

75. The method of claim 67, wherein the at least one of examining and treating of ocular tissue comprises using a laser.

76. The method of claim 75, wherein the laser comprises a laser photocoagulator.

77. The method of claim 75, wherein the laser comprises a laser photodisrupter.

78. The method of claim 67, wherein the liquid is contained within a bag.

79. A method for at least one of examining and treating ocular tissue, comprising:

attaching a transparent, malleable material to a lens of a microscope;

contacting the malleable material with a cornea such that the malleable material conforms to a natural shape of the cornea; and at least one of examining and treating ocular tissue by light transmission through the malleable material.

80. A multi-layered contact lens element for at least one of examination and treatment of ocular tissues, comprising a plurality of lens elements in layers including a first lens element having a recess capable of forming a substantially enclosed space with a cornea of an eye to be examined or treated, the substantially enclosed space being capable of being filled with a liquid, and wherein at least one surface of each lens element of the plurality of lens elements contacts a surface of another lens of the plurality of lens elements.

81. A contact lens element for at least one of examination and treatment of ocular tissues, comprising a concave surface capable of contacting a cornea of an eye to be examined or treated having a radius of curvature that is less than approximately a radius of curvature of the cornea and having a diameter of about 7 to 12 mm, and an exterior convex surface having a diameter of about 13 to 19 mm, the contact lens element having a thickness of about 8 to 20 mm, wherein the contact lens element includes a vent.

82. A system for at least one of examination and treatment of ocular tissues, comprising:

an optically clear liquid having a refractive index greater than 1.338; and a contact lens element capable of forming a substantially enclosed space with a cornea of an eye to be examined or treated, the substantially enclosed space being capable of being filled with the liquid, and wherein the contact lens element comprises at least one hole for filling the liquid.

* * * * *

UNITED STATES PATENT AND TRADEMARK OFFICE
CERTIFICATE OF CORRECTION

PATENT NO. : 6,019,472
DATED : February 1, 2000
INVENTOR(S) : C.J. KOESTER et al.

It is certified that error appears in the above-identified patent and that said Letters Patent is hereby corrected as shown below:

On the cover of the printed patent, at Item [56], References Cited, Other Publications, line 8, "Objecxtive" should be ---Objective---

At column 22, line 50 (claim 17, line 9) of the printed patent, after "liquid" insert --- , ---.

Signed and Sealed this

Fifteenth Day of May, 2001

Attest:

NICHOLAS P. GODICI

Attesting Officer

Acting Director of the United States Patent and Trademark Office